(12) United States Patent  
Aptaker et al.

(10) Patent No.: US 7,064,548 B2
(45) Date of Patent: Jun. 20, 2006

(54) RF PROBE APPARATUS FOR NMR CHECK WEIGHING SYSTEM

(75) Inventors: Peter Aptaker, Letcombe Basset (GB); Robert Selway, Kidlington (GB); Paulus C. J. M. Hendrickx, Baarle-Nassau (NL); Jozef A. W. M. Corver, Nuenen (NL); Vincent Bons, Hamburg, NY (US)

(73) Assignee: The BOC Group, Inc., Murray Hill, NJ (US)

( * ) Notice: Subject to any disclaimer, the term of this patent is extended or adjusted under 35 U.S.C. 154(b) by 0 days.

(21) Appl. No.: 10/836,844

(22) Filed: Apr. 30, 2004

(65) Prior Publication Data

US 2005/0242813 A1 Nov. 3, 2005

(51) Int. Cl.
*G01V 3/00* (2006.01)

(52) U.S. Cl. ..................... 324/318; 324/321
(58) Field of Classification Search ............. 324/306, 324/307, 308, 309, 318, 322
See application file for complete search history.

(56) References Cited

U.S. PATENT DOCUMENTS

| | | | |
|---|---|---|---|
| 3,796,873 A | | 3/1974 | Ledgett |
| 4,584,548 A | * | 4/1986 | Inoue et al. ............. 335/299 |
| 4,727,325 A | | 2/1988 | Matsui et al. |
| 4,884,696 A | * | 12/1989 | Peleg ..................... 209/545 |
| 5,015,954 A | | 5/1991 | Dechene et al. |
| 5,049,819 A | | 9/1991 | Dechene et al. |
| 5,291,422 A | | 3/1994 | Esztergar |
| 5,302,894 A | | 4/1994 | Hrubes |
| 5,302,896 A | * | 4/1994 | Dechene et al. ........... 324/307 |
| 5,302,897 A | * | 4/1994 | Tache et al. ............. 324/307 |
| 5,367,260 A | * | 11/1994 | Dechene et al. ........... 324/307 |
| 5,408,181 A | * | 4/1995 | Dechene et al. ........... 324/307 |
| 5,530,350 A | * | 6/1996 | Dechene et al. ........... 324/306 |
| 5,596,275 A | * | 1/1997 | Dechene et al. ........... 324/307 |

(Continued)

FOREIGN PATENT DOCUMENTS

DE 1803372 A1 5/1970

(Continued)

OTHER PUBLICATIONS

Derwent WPI Abstract, UNILEVER NV, Package Weight Measuring System, NL 154001B, Jul. 15, 1977 (Corresponds to DE 1803372A1).

*Primary Examiner*—Diego Gutierrez
*Assistant Examiner*—Tiffany A. Fetzner
(74) *Attorney, Agent, or Firm*—Ira L. Zebrak; Bernard Lau

(57) ABSTRACT

A radio frequency (RF) probe (10) for a nuclear magnetic resonance check weighing system produces a uniform magnetic field at the center of RF probe (10), has minimal sensitivity to electrical interference from external sources, shapes the magnetic field to minimize cross coupling from packages such as drug vials (22) not under test, and presents minimal airflow obstruction. RF probe (10) includes a coil (100) with a plurality of conductive loops (102, 104) having a rectangular cross section carried inside two opposing, rectangular cross section housings (106, 108), respectively. Housings (106, 108) are spaced apart and in parallel, creating an "open probe" configuration permitting a conveyor belt (28) carrying vials (22) whose contents are to be checked to pass between housings (106, 108), and allows airflow surrounding the vials (22) and conveyor belt (28) to pass substantially without obstruction. Conductive loops (102, 104) and the housings (106, 108) carrying them may be placed such that the longitudinal axis of coil (100) is oriented in either horizontal or vertical spatial relation with conveyor belt (28).

10 Claims, 4 Drawing Sheets

U.S. PATENT DOCUMENTS

| | | | |
|---|---|---|---|
| 5,684,399 A * | 11/1997 | Bayer | 324/306 |
| 5,966,457 A * | 10/1999 | Lemelson | 382/141 |
| 6,028,428 A | 2/2000 | Cunningham et al. | |
| 6,362,619 B1 | 3/2002 | Prammer et al. | |
| 6,377,049 B1 | 4/2002 | Benz et al. | |
| 6,426,058 B1 | 7/2002 | Pines et al. | |
| 6,479,994 B1 * | 11/2002 | Hills et al. | 324/306 |
| 6,549,007 B1 * | 4/2003 | Hills et al. | 324/306 |
| 6,556,013 B1 | 4/2003 | Withers | |
| 6,556,873 B1 * | 4/2003 | Smits | 607/122 |
| 6,759,601 B1 * | 7/2004 | Petty et al. | 177/1 |
| 6,842,004 B1 | 1/2005 | Withers et al. | |
| 6,946,838 B1 * | 9/2005 | Corver et al. | 324/307 |
| 7,002,346 B1 * | 2/2006 | Schaepman et al. | 324/315 |
| 7,015,693 B1 * | 3/2006 | Corver et al. | 324/300 |
| 2004/0231699 A1 | 11/2004 | Corver | |
| 2004/0251904 A1 | 12/2004 | Corver et al. | |
| 2005/0116712 A1 * | 6/2005 | Corver et al. | 324/309 |
| 2005/0122104 A1 * | 6/2005 | Corver et al. | 324/309 |
| 2005/0242808 A1 * | 11/2005 | McKendry et al. | 324/307 |
| 2005/0242809 A1 * | 11/2005 | McKendry et al. | 324/308 |
| 2005/0242811 A1 * | 11/2005 | Schaepman et al. | 324/315 |
| 2005/0242813 A1 * | 11/2005 | Aptaker et al. | 324/318 |
| 2005/0247493 A1 * | 11/2005 | Aptaker et al. | 177/1 |

FOREIGN PATENT DOCUMENTS

| | | |
|---|---|---|
| GB | 2149509 A | 6/1985 |
| WO | WO 99/67606 A1 | 12/1999 |
| WO | WO 2004104600 A2 * | 12/2004 |

* cited by examiner

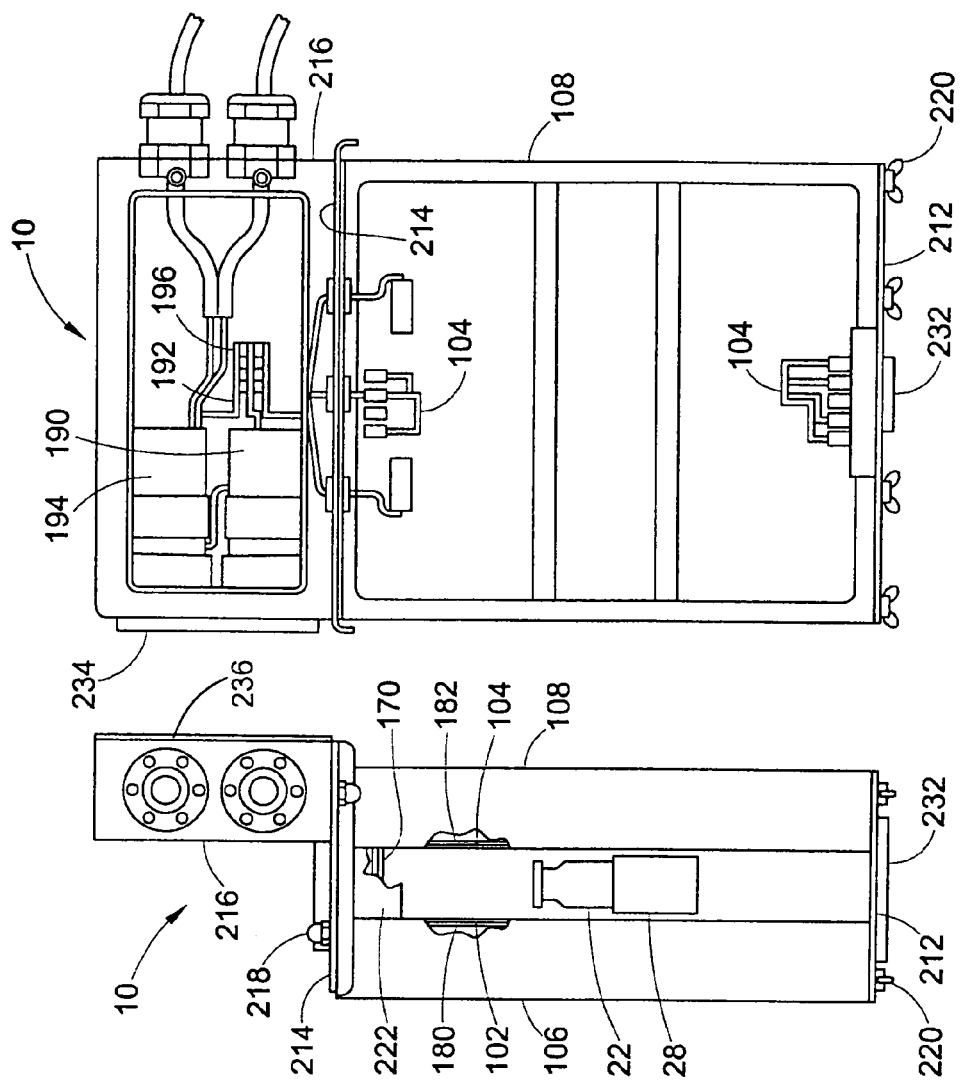
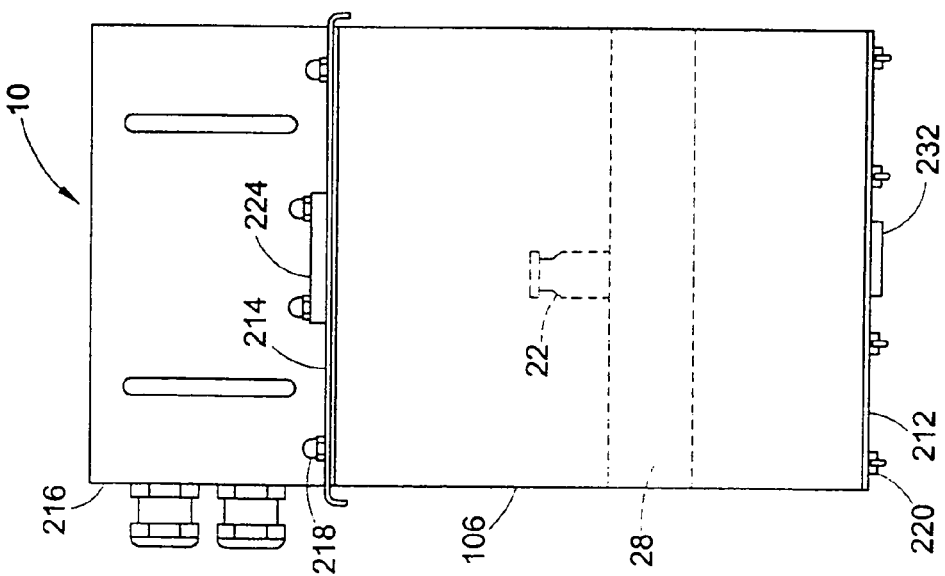

RF PROBE APPARATUS FOR NMR CHECK WEIGHING SYSTEM

FIELD OF THE INVENTION

The present invention relates to check weighing material in a container, while the container is moving in a production line, using nuclear magnetic resonance (NMR) techniques. More particularly, the present invention relates to a RF probe apparatus for an NMR check weighing system.

BACKGROUND

The use of NMR techniques in measurement, detection and imaging has become desirable in many scientific fields of endeavor. The non-invasive, non-destructive nature of NMR has facilitated application to industrial instrumentation, analysis and control tasks, in a variety of applications, including but not limited to cosmetics, perfumes, industrial chemicals, biological samples and food products. As one example, check weighing is used by the pharmaceuticals industry for monitoring and regulating the amount of drug in a sealed glass vial during filling. The drug weight can be as small as a fraction of a gram, and is required to be weighed with an accuracy of a few percent or better, in a vial weighing tens of grams at a rate of several weighing per second.

International Patent Application No. WO99/67606, incorporated herein by reference as if fully written out below, describes a check weighing system for samples on a production line using NMR techniques. This system includes a magnet for creating a static magnetic field over an interrogation zone to produce a net magnetisation within a sample located within the interrogation zone, and a RF coil for applying an alternating magnetic field over the interrogation zone to cause excitation of the sample according to the principles of NMR.

As is well known in the general NMR art, successful application of magnetic resonance requires that the RF coil generate a uniform magnetic field at the location of the sample protons under test, and that the RF coil have minimal sensitivity to electrical interference (i.e., noise) from external sources. A variety of basic RF coil configurations have been utilized in NMR systems to satisfy these constraints, including helical, saddle and Helmholz. However, in continuous production line applications additional constraints make such shapes unusable.

For example, in continuous production line applications where a plurality of closely proximate packages move continuously, the field produced by the RF coil at the site of packages neighboring the sample under test must be minimized to avoid influencing the field and measurement of the sample under test (i.e., reduce cross coupling). This is a significant concern in applications such as the packaging of pharmaceuticals where rows of drug vials move simultaneously down the production line.

Pharmaceutical packaging is also exemplary of another significant constraint upon RF probes. Clean environmental restrictions require the unimpeded airflow in the vicinity of the vials, and any RF probe utilized in this application must be designed for minimal airflow obstruction.

It is desirable to provide a RF probe apparatus for an NMR check weighing system that produces a uniform magnetic field at the test location (preferably the center of the RF probe), has minimal sensitivity to electrical interference from external sources, shapes the magnetic field to minimize cross coupling from packages not under test, and presents minimal airflow obstruction.

SUMMARY

There is provided apparatus for applying an alternating magnetic field in an interrogation zone of a magnetic resonance measurement for determining the mass of samples in a production line having a direction of travel, comprising:

a first plurality of coil elements substantially in a first plane in spatial relation with the production line; and, a second plurality of coil elements substantially in a second plane, said second plurality of coil elements electrically connected to, and in spatial relation with said first plurality of coil elements, said second plurality of coil elements separated from said first plurality of coil elements allowing the samples in the production line to pass through the separation of said first plurality of coil elements and said second plurality of coil elements.

There is also provided a radio frequency probe for magnetic resonance measurement for determining the mass of samples in a production line having a direction of travel, comprising:

a first plurality of coil elements substantially in a first plane in spatial relation with the production line; and, a second plurality of coil elements substantially in a second plane, said second plurality of coil elements electrically connected to, and in one of substantially parallel and perpendicular spatial relation to the production line planar direction of travel, said second plurality of coil elements separated from said first plurality of coil elements allowing the samples in the production line and airflow thereabout to pass through the separation of said first plurality of coil elements and said second plurality of coil elements substantially unobstructed.

BRIEF DESCRIPTION OF THE DRAWINGS

FIG. 6 is a front elevational view of an exemplary RF probe apparatus in accordance with the present invention showing in phantom a vial and conveyor belt passing through the RF probe.

FIG. 7 is a right side elevational view of the exemplary RF probe shown in FIG. 5 showing a vial passing through the RF probe.

FIG. 8 is a rear elevational view of the exemplary RF probe shown in FIG. 5.

DETAILED DESCRIPTION

Figure 1:
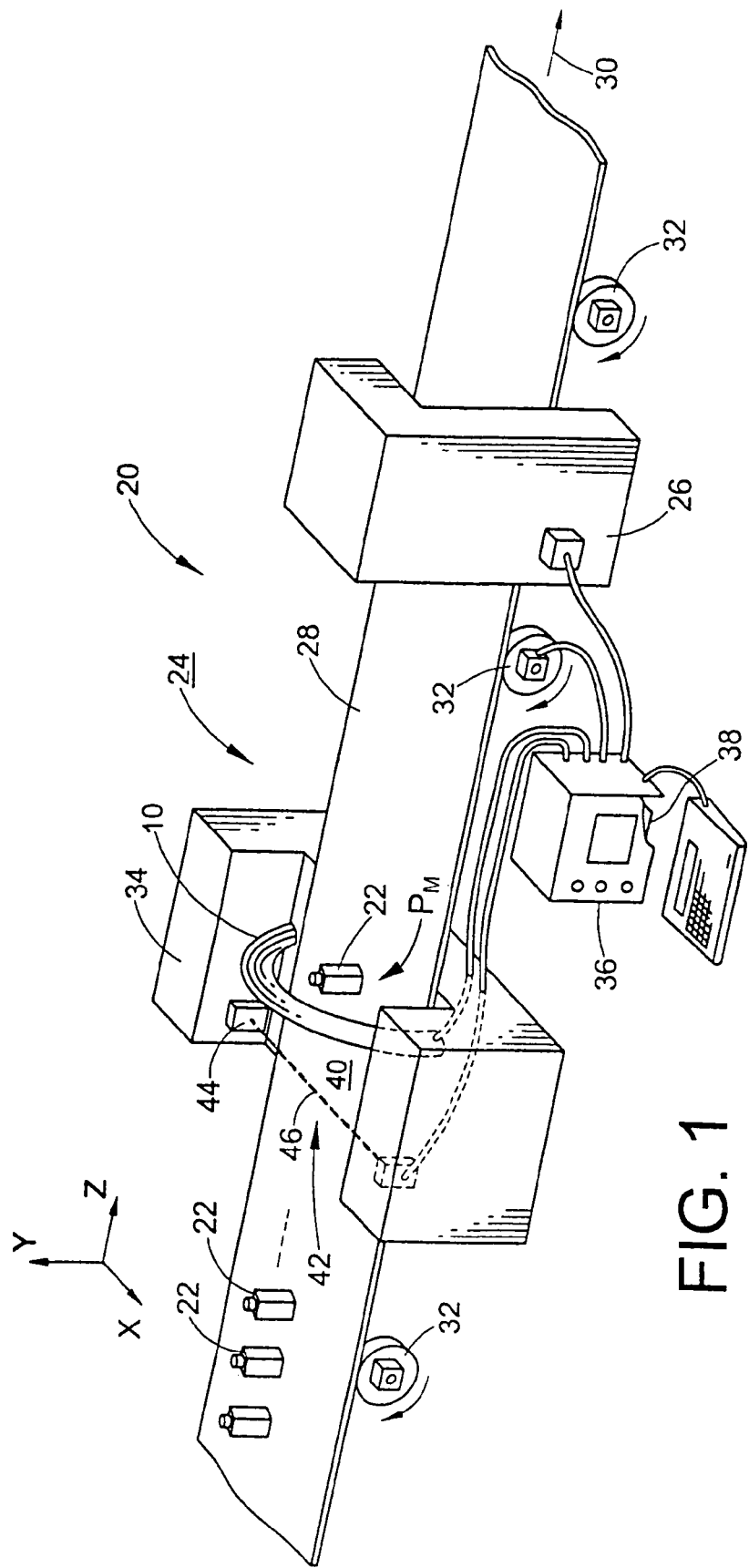
FIG. 1 is a perspective view of a portion of a production line with an exemplary NMR check weighing station for checking that each container passing through the weighing station has the desired amount of product.

An exemplary RF probe apparatus in accordance with the present invention is indicated generally by the numeral 10 in FIG. 1 and FIG. 5 through FIG. 8. As best seen in FIG. 1, RF probe 10 is used in a non-contact, NMR check weighing system 20 to check the mass (or weight) of the content of a container while continuously moving in a production line. One exemplary application requiring such check weighing is the packaging of pharmaceuticals.

Exemplary NMR Check Weighing System for Pharmaceutical Packaging

FIG. 1 shows a portion of a production line, which fills glass vials 22 with a drug sample. The exemplary check weighing station 24 is provided "in-line" for non-contact weighing of each of the filled vials that pass therethrough, and a reject station 26 that removes those vials from the line that do not have the sufficient amount of the drug to meet product specifications. Vials 22 including their non-continuous and discrete samples are transported to check weighing station 24 from a filling (and optionally sealing) station (not shown) by a conveyor having a conveyor belt 28 which, as represented by the arrow 30, moves along the conveyor's longitudinal axis in the z direction through the action of rotating conveyor wheels 32.

Check weighing station 24 uses NMR techniques to determine the mass of the drug sample within each of the vials 22. As those ordinarily skilled in the art will appreciate, glass vials are useful as the container, because they do not give a signal that might interfere with the measurement process. In this embodiment, check weighing station 24 includes a permanent magnet 34, RF probe 10 (shown diagrammatically in FIG. 1), and a computer control system 36 having a processor 38. Magnet 34 creates a homogeneous direct current (DC) or static magnetic field in the x direction across conveyor belt 28 in a region that may be referred to as the interrogation zone 40. Interrogation zone 40 extends the length of conveyor belt 28 through which the static magnetic field is uniformly applied by permanent magnet 34. The sample in vial 22 contains nuclei which each possess a magnetic moment, e.g. 1H nuclei (protons), as a result of the spin of the nuclei. Because the sample protons posses a magnetic moment, the sample is capable of acquiring a net magnetisation when under the influence of certain magnetic fields. When the sample is within interrogation zone 40, the applied static magnetic field creates a net magnetisation within the sample. A vial position detection device 42 preceding or at the start of interrogation zone 40 (such as the optical position sensor 44 having a light beam 46) accurately and precisely detects when vial 22 reaches a known physical position on conveyor belt 28 preceding check weighing station 24.

In most NMR systems, the static magnetic field strength is such that the Larmor frequency of the sample is in the radio frequency range of the electromagnetic spectrum. Applying an alternating current (AC) magnetic field to the sample at the sample's Larmor frequency and orientated orthogonal to the static magnetic field, will cause the sample's net magnetisation to rotate about the AC magnetic field's axis, away from the direction of the static field. In this embodiment, this magnetic field is generated by applying a corresponding AC current to the RF probe 10. Varying the amount of energy delivered to the RF probe 10 can vary the angle of rotation of the net magnetisation.

In this exemplified embodiment, an excitation field that causes a 90° rotation is used to excite the sample. After the 90° pulse has been applied to the sample, the sample is left in a high-energy, non-equilibrium state, from which it will relax back to its original state of equilibrium. As it relaxes, electromagnetic energy at the Larmor frequency is emitted, the magnetic component of which induces a sample reply signal in the form of current in the RF probe 10.

RF probe 10 monitors energy emitted by the sample as the net magnetisation of the sample returns to its original state and generates an output signal having a characteristic which is proportional to the energy emitted. In the present example a characteristic of the induced current, i.e., amplitude, varies with, among other things, the number of magnetic moments in the sample and hence the number of molecules in the sample. The received signal is then passed to the computer control system 36, which compares the amplitude of the signal received from the unknown sample, with the amplitude of a signal received from a calibration sample with a known mass (or weight), to determine the mass (or weight) of the sample being tested. The check weighing station 24 may be able to generate and receive signals at different Larmor frequencies needed to be able to excite different NMR responsive elements in samples. If the computer control system 36 can store calibration data for each of the different samples, then the check weighing station would be able to determine the mass of various samples using a characteristic of the NMR signals from the different NMR responsive elements.

For illustrative purposes, but not by way of limitation, the general operation of the NMR check weighing system 24 as shown in FIG. 1 will be described. First, check weighing system 24 is initialized, including installing a RF probe 10 appropriate for the sample to be tested. Once production is begun, conveyor belt 28 continuously transports vials 22 whose sample mass (or weight) is to be determined. As each vial 22 reaches a position detected by optical position sensor 44, optical position sensor 44 generates a signal accurately establishing the position of that vial 22 to computer control system 36. Computer control system 36 then tracks the motion of conveyor belt 28 as vial 22 advances to the position $P_M$, within interrogation zone 40 where the sample in vial 22 will return the maximum sample reply signal.

At the instant in time when vial 22 is in position $P_M$, a brief energization of RF probe 10 is triggered, applying an alternating magnetic field in interrogation zone 40 such that the net magnetisation of the sample in vial 22 is temporarily changed. RF probe 10 monitors the energy emitted by the sample in vial 22 as the net magnetisation of the sample returns to its original state of equilibrium, and generates an output signal having a characteristic which is proportional to the energy emitted, such as current amplitude. Computer control system 36 receives the RF probe 10 output signal. Processor 38 compares the current amplitude or other output signal characteristic with like data obtained from at least one similar sample of known mass, and determines the mass of the sample from the results of the comparison.

RF Probe

Figure 2:
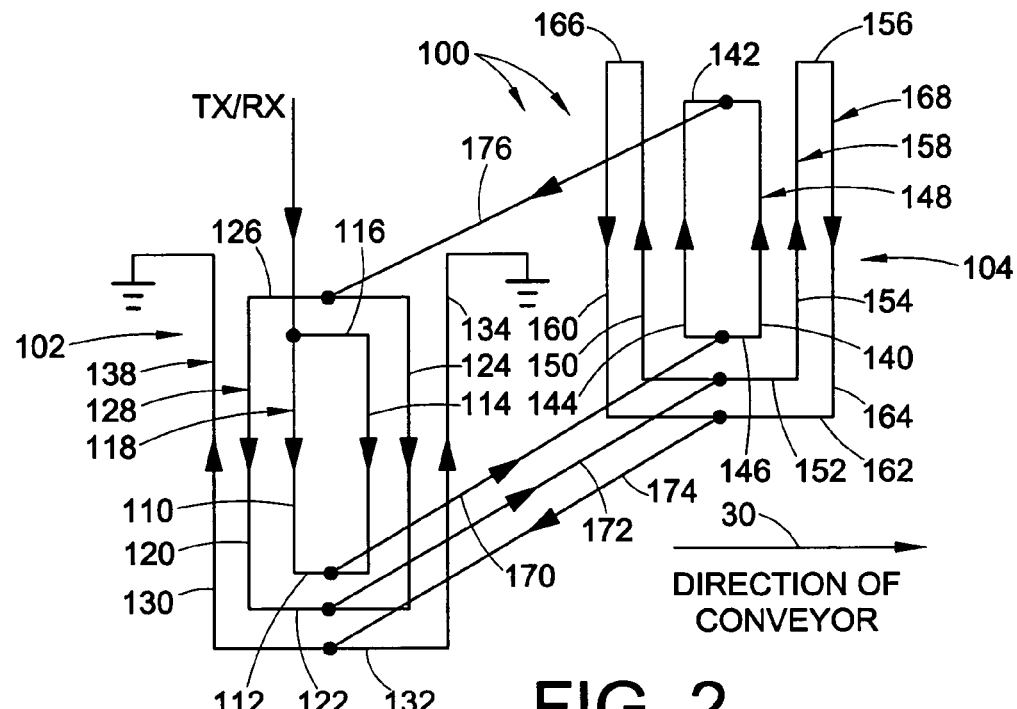
FIG. 2 is a schematic diagram of the current conducting path in an exemplary RF probe apparatus in accordance with the present invention.
Figure 3:
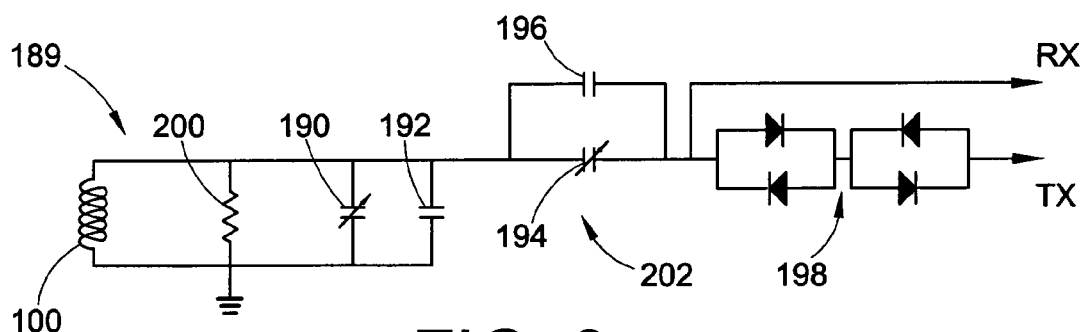
FIG. 3 is an electrical circuit diagram of an exemplary resonant circuit for the exemplary RF probe apparatus shown in FIG. 1. In the resonant circuit shown in this figure, the capacitors are electrically connected in a series configuration.
Figure 4:
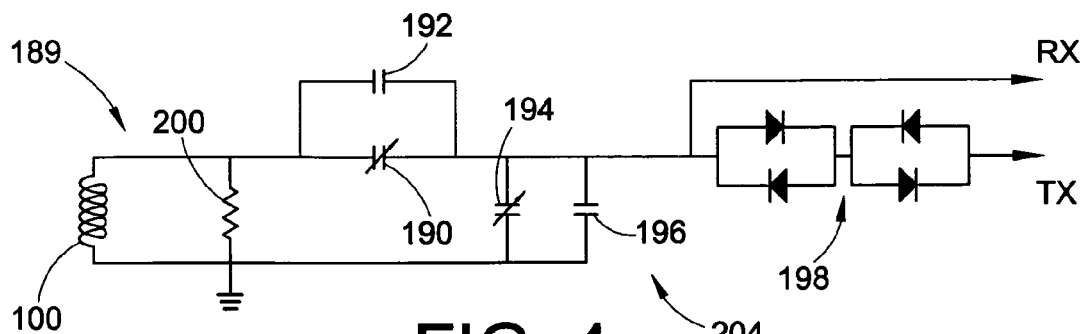
FIG. 4 is an electrical circuit diagram of an exemplary resonant circuit for the exemplary RF probe apparatus shown in FIG. 1. In the resonant circuit shown in this figure, the capacitors are electrically connected in a shunt configuration.
Figure 5:
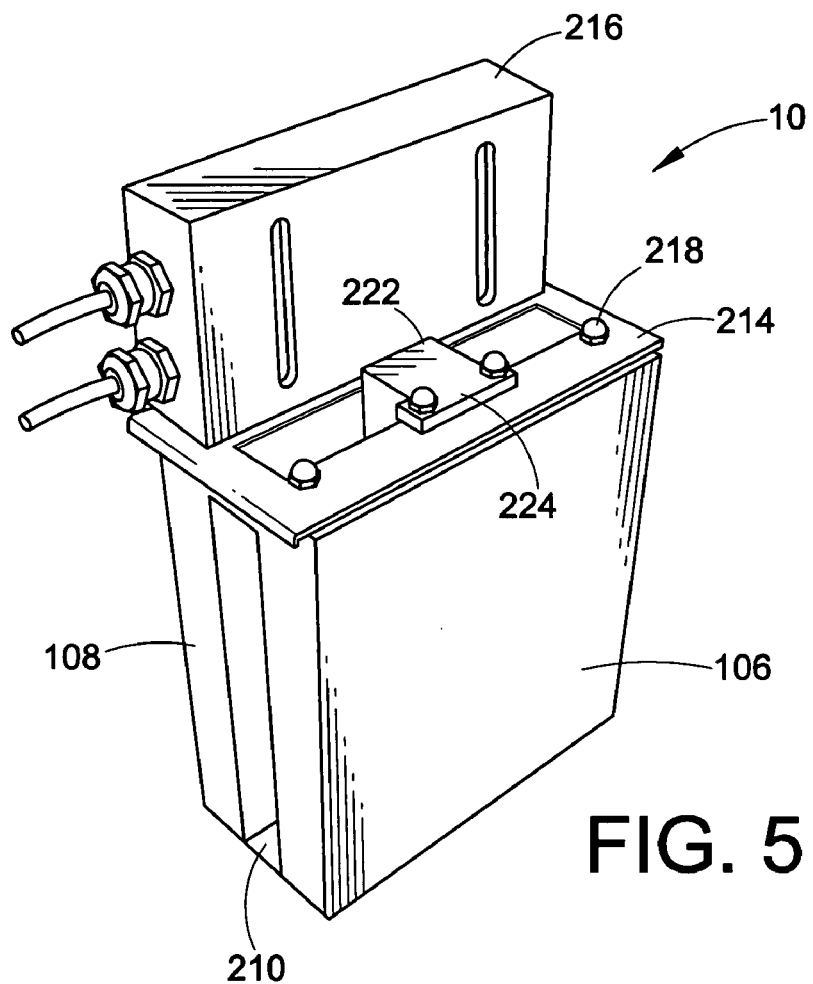
FIG. 5 is a perspective view of an exemplary RF probe apparatus in accordance with the present invention.
Figure 9:
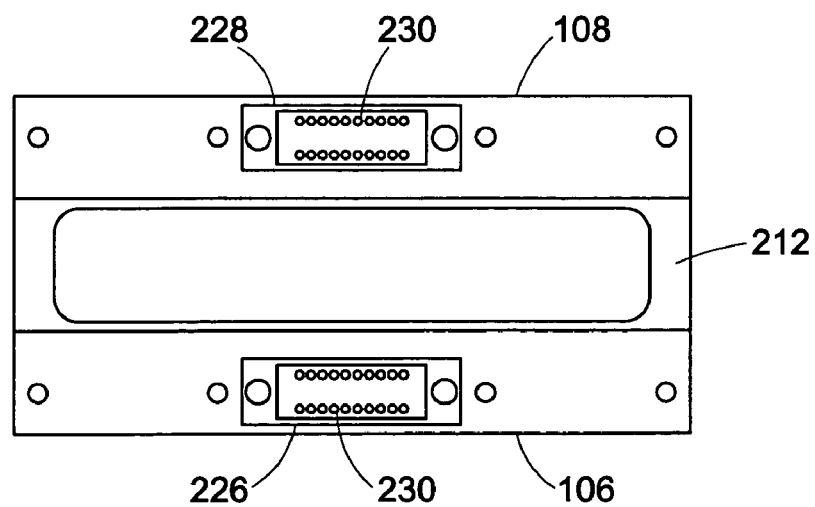
FIG. 9 is a bottom view of the exemplary RF probe shown in FIG. 5.

An exemplary RF probe 10 in accordance with the present invention is best illustrated electrically in FIGS. 2 through 4, and mechanically in FIGS. 5 through 9. More specifically, FIG. 2 presents a schematic diagram of the RF probe 10 current conducting path, FIGS. 3 and 4 show an electrical circuit diagram of two forms of an exemplary RF probe 10 resonant circuit, and FIGS. 5 through 9 depict perspective, front elevational, right side elevational, rear elevational and bottom views of the physical form of RF probe 10.

As best seen in FIGS. 2 through 5, an RF probe 10 in accordance with the present invention includes a coil 100 with a plurality of conductive loops 102 and 104 that operate substantially simultaneously, and which have a rectangular cross section retained inside two opposing, rectangular cross section housing sides to RF probe 10 or housings 106 and 108, respectively. The housings 106,108 are spaced apart and in parallel, creating an "open probe" configuration. The open probe configuration permits conveyor belt 28 carrying the vials 22 whose contents are to be checked to pass between housings 106 and 108, and allows airflow surrounding the vials 22 and conveyor belt 28 to pass substantially without obstruction. The conductive loops 102, 104 and the housings 106,108 carrying them may be placed such that the longitudinal axis of coil 100 is oriented in either horizontal or vertical spatial relation with conveyor belt 28.

The conductive loops 102 in housing 106 and the conductive loops 104 in housing 108 are electrically connected to present electromagnetically a single, continuous coil 100 having a plurality of substantially planar coil elements. The detailed current conducting path is illustrated in FIG. 2, with reference to the direction of movement 30 of the conveyor. Conductive loops 102 include a plurality of coil elements 110, 112, 114 and 116 formed into inner loop 118, coil elements 120, 122, 124 and 126 formed into inner loop 128, and coil elements 130, 132, and 134 formed with a connection to ground at the open end of coil elements 130 and 134 into outer loop 138. Similarly, conductive loops 104 include a plurality of coil elements 140, 142, 144 and 146 formed into inner loop 148, coil elements 150, 152 and 154 with reverse turn coil element 156 formed into inner loop 158, and coil elements 160, 162 and 166 with reverse turn 168 formed into an outer, reverse turn loop 168.

Four conductors electrically connect conductive loops 102 and 104 in different housings 106 and 108, respectively. Conductor 170 electrically connects inner loops 118 and 148; conductor 172 electrically connects inner loops 128 and 158; conductor 174 electrically connects outer loops 138 and 168; and conductor 176 electrically connects inner loops 128 and 148.

The conductive path is shown with arrows on each vertical coil element and each conductor. The path may be seen to begin with the node where one end of coil elements 110 and 116 are electrically connected to each other and the transmitter output and receiver input TX/RX, and sequentially travels through inner loop 118, conductor 170, inner loop 148, conductor 176, inner loop 128, conductor 172, inner loop 158, reverse turn loop 168, conductor 174, outer loop 138, and ground back to the transmitter output and receiver input.

The skilled artisan will understand that the number of forward and reverse turns will vary depending the size of coil needed for package size. In the present example a RF coil 10 having two forward and one reverse polarity loops has been found to be optimal for the size associated with a 2 ml volume drug vial 22. The skilled artisan will further appreciate that these reverse polarity turn or turns at the ends of coil 100 actively shape the alternating magnetic field perimeter to minimize cross coupling effects from samples neighboring the sample under test, i.e., minimize the alternating magnetic field at vials 22 positions other than that of the sample under test, preferably the center of RF probe apparatus 10. Alternatively or additionally, the alternating magnetic field perimeter may be passively shaped for the same purpose by inclusion of shaping coils 180 and 182.

Shaping coils 180, 182 may be formed with electrically connected coil elements as was used for conductive loops 102 and 104 and are similarly include in housings 106, 108 at the ends of coil 100.

RF probe 10 includes a resonant circuit 189 to generate the necessary short pulse of an alternating magnetic field at the frequency of interest. Exemplary, suitable resonant circuits include those shown in FIGS. 3 and 4. In FIG. 3 coil 100 has electrically connected in parallel across its terminals an adjustable tuning capacitor 190 having a user adjustable capacitance, and one or more fixed capacitance tuning capacitors 192. Tuning capacitors 190, 192 set and adjust the resonance frequency of RF coil 10. An adjustable matching capacitor 194 and one or more fixed capacitance matching capacitors 196 electrically connected in parallel therewith, are electrically connected in series between one end of coil 100 and both the receiver (not shown) and transmitter (not shown) for NMR check weighing system 20. The Matching capacitors 194, 196 match the impedance of the loaded RF probe 10 to that of the characteristic impedance (usually 50 ohms) of the cable coming from the receiver RX and transmitter TX. A four diode network 198 in series between the transmitter and the matching capacitors 194, 196 isolate the receiver from the transmitter whose power might otherwise oversaturate the receiver. An optional shunt resistor 200 may be placed across coil 100 to dissipate any stored energy when NMR check weighing system 20 is not in use.

The resonant circuit configuration shown in FIG. 3 is commonly referred to as a series resonant circuit 202. In FIG. 4, the electrical connection of tuning capacitors 190, 192 and matching capacitors 194, 196 are interconnected in what is commonly referred to as a shunt resonant circuit 204.

As will be explained in further detail below, important additional alternating magnetic field shaping and interference minimization may be achieved by coating the inside face of each housing 106, 108 with an electrically conductive material, such as copper. When coil 100 is energized, eddy currents are induced in this conductive coating that help to shape the alternating magnetic field perimeter and minimize cross coupling and other external interference.

FIGS. 5 through 9 best illustrate the mechanical aspects of the exemplary RF probe 10 described herein for application to determination of the mass of the content of 2 ml drug vials 22. From a general mechanical vantage, RF probe 10 includes the two parallel, substantially rectangular housings 106 and 108 in spatial relation to provide a passageway 210 therebetween, a flat bottom plate 212 joining housings 106, 108 at their bottom, a flat, removable top plate 214 joining housings 106, 108 at their top, and a capacitor box 216 mounted on one side of top plate 214.

Housings 106, 108 and passageway 210 are sized to allow conveyor belt 28, all vials 22 thereon and the airflow therearound, pass unobstructed through the center of RF coil 10, the preferred site of the sample under test where the magnetic fields are most uniform. In the present example, where conveyor carries multiple rows of 2 ml vials 22, housings 106, 108 of about 20 cm high, 20 cm wide and 10 cm deep with a passageway of about 10 cm have been found to be appropriate. Both bottom plate 212 and top plate 214 may have a substantial open aperture formed therein to further facilitate unobstructed airflow.

The ordinarily skilled user understands that RF probe 10 must be configured and optimized for each unique package volume and dimension. Thus, it may be desirable to make RF probe 10 easily removable and installable by the user so conveyor belt 28 may be used for a variety of packages. To this end components joining the bottom of housings 106 and 108 may be made easily removable. Accordingly, while top plate 214 may be affixed to housings 106, 108 using threaded bosses and cap nuts 218, bottom plate 212 may be affixed using threaded bosses and wing nuts 220.

Conductors 170, 172, 174 and 176 and ground connections must pass between coil elements in housings 106 and 108 as explained above. In the present example, three of those conductors are shown passing therebetween at the top of housings 106 and 108 just below top plate 214. A substantially U-shaped channel 222 having a flange 224 for mounting to the threaded bosses of top plate 214 may be provided to protect the conductors passing at the top of housings 106 and 108, and facilitate airflow and spacing therebetween. Other conductors may be electrically connected through two multiple pin block connectors 226 and 228, having a plurality of pins 230 suitable to pass the high frequency current conducted in conductive loops 102 and 104, that are mounted in the bottom of housings 106 and 108, respectively. A mating bridge connector 232 removeably engages and electrically connects pins 230 within block connectors 226 and 228.

Capacitor box 216 carries the resonant circuit components described above in connection with FIGS. 2 and 3. Adjustment of tunable capacitors 190 and 194 is provided by means of a removable cover 234 providing access to the rotatable shafts of capacitors by which changes of their capacitance value may be effected by the user. Another removable cover 236 provides access to the interior of capacitor box 216. All removable covers are preferably provided with silver loaded VITON® elastomer "O" ring seals, to improve both RF and airtight sealing. The interior of capacitor box is preferably coated with a conductor such as copper for improved RF screening. Capacitor box 216, as discussed above, is positioned above and attached to housing 108. While this asymmetric mounting often exacerbates noise, in the present application it was found to be desirable to maximize airflow.

The radio frequency response in NMR check weighing system 20 is critically dependent on a variety of factors and can deleteriously impact the NMR measurement. Accordingly, materials from which a RF probe 10 are fabricated must be carefully selected to provide low magnetic properties and interaction, ease of manufacture, cost minimization, and availability. Additionally, in a pharmaceutical application, all materials must be compatible with the environmental requirements mentioned above. So, for example, materials selected for housings 106 and 108 must be able to withstand the cleaning agents used and not discolor or mechanically degrade.

Materials found acceptable for use with RF probe 10 include 316 grade or better stainless steel for housings 106 and 108, capacitor box 216, bottom plate 212, top plate 214 and all removable covers. All interior surfaces and stud bosses should be plated with a suitable RF shield conductor such as copper and gold. Acceptable printed circuit board material was found in DICLAD™ 880 woven fiberglass reinforced polytetrafluoroethylene. Connector blocks and capacitor standoffs successfully used acetyl, commercially called DELRIN® acetal resin. Channel 222 is optimally manufactured from Polytetrafluoroethylene (PTFE).

It will be understood that the embodiments described herein are merely exemplary and that a person skilled in the art may make many variations and modifications without departing from spirit and scope of the invention. The various embodiments may be practiced in the alternative, or in combination, as appropriate. All such modifications and variations are intended to be included within the scope of the invention as defined in the appended claims.

We claim:

1. Radio frequency apparatus configured for use in a magnetic resonance check weighing system in order to determine the mass of non-continuous and discrete samples in a production line where the production line has a longitudinal axis, comprising:
    a radio frequency probe including a first plurality of substantially planar coil elements and a second plurality of substantially planar coil elements;
    a housing including:
        a first side retaining said first plurality of substantially planar coil elements substantially in a first plane, along the longitudinal axis of the production line and
        a second side retaining said second plurality of substantially planar coil elements substantially in a second plane different from said first plane, which is also along the longitudinal axis of the production line;
    said housing having a passageway between said first side retaining said first plurality of substantially planar coil elements and said second side retaining said second plurality of substantially planar coil elements through which the non-continuous and discrete samples may pass; and
    wherein said first plurality of substantially planar coil elements are electrically connected to, and in spatial relation with said second plurality of substantially planar coil elements.

2. An apparatus according to claim 1, wherein said second plurality of substantially planar coil elements is in further spatial relation with said first plurality of substantially planar coil elements allowing airflow in proximity to the samples in a production line to pass substantially without obstruction through the passageway.

3. An apparatus according to claim 1, wherein the production line has a planar direction of travel, and the spatial relation of said second plurality of substantially planar coil elements and said first plurality of substantially planar coil elements is one of substantially parallel and perpendicular to the planar direction of travel of the production line.

4. An apparatus according to claim 3, wherein said first plurality of substantially planar coil elements is substantially parallel to said second plurality of substantially planar coil elements.

5. An apparatus according to claim 1, wherein said coil elements of said first plurality of substantially planar coil elements and said coil elements of said second plurality of substantially planar coil elements are each formed into a plurality of conductive loops.

6. An apparatus according to claim 5, wherein said plurality of conductive loops are substantially rectangular in shape.

7. An apparatus according to claim 6, wherein said radio frequency probe applies an alternating magnetic field in an interrogation zone and said plurality of conductive loops are arranged substantially one inside another, and said coil elements forming the outermost conductive loop are electrically connected so that the current passing therethrough is in reverse polarity from the polarity of the current passing through the inner conductive loops so as to shape the alternating magnetic field perimeter to minimize cross coupling effects by neighboring samples.

8. An apparatus according to claim 6, wherein said radio frequency probe applies an alternating magnetic field in an interrogation zone and said plurality of conductive loops are arranged substantially one inside another, the apparatus further including a first passive shading coil in operative association with the outermost conductive loop formed from said first plurality of substantially planar coil elements and a second passive shading coil in operative association with the outermost conductive loop formed from said second plurality of substantially planar coil elements.

9. An apparatus according to claim 6, wherein said radio frequency probe applies an alternating magnetic field in an interrogation zone and said conductive loops are arranged substantially one inside another, and the spacing of said coil elements forming the innermost conductive loop includes a gap larger than the spacing of said coil elements forming other conductive loops so as to increase the uniformity of the alternating magnetic field at its center.

10. An apparatus according to claim 1, wherein the electrically connected said first plurality of substantially planar coil elements and said second plurality of substantially planar coil elements form a single coil having a continuous electrically conductive path, and further including a resonant circuit electrically connected to said single coil and forming a magnetic resonance radio frequency probe.

* * * * *